(12) United States Patent
Dawes et al.

(10) Patent No.: US 8,721,971 B2
(45) Date of Patent: May 13, 2014

(54) NOX ADSORPTIVE FILMS FOR NOX SENSOR TECHNOLOGIES

(75) Inventors: Steven Bruce Dawes, Corning, NY (US); Zhiqiang Shi, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 74 days.

(21) Appl. No.: 12/393,821

(22) Filed: Feb. 26, 2009

(65) Prior Publication Data

US 2010/0215546 A1 Aug. 26, 2010

(51) Int. Cl.
*G01N 15/06* (2006.01)

(52) U.S. Cl.
USPC .............. 422/98; 422/50; 422/83; 422/88

(58) Field of Classification Search
USPC .......................................... 422/50, 83, 88, 98
See application file for complete search history.

(56) References Cited

U.S. PATENT DOCUMENTS

| | | | |
|---|---|---|---|
| 5,364,797 A | 11/1994 | Olson et al. | 436/501 |
| 6,395,350 B1 * | 5/2002 | Balkus et al. | 427/556 |
| 7,112,237 B2 | 9/2006 | Zeller et al. | 95/273 |
| 7,194,891 B2 | 3/2007 | Tuller et al. | 73/24.01 |
| 7,287,370 B2 | 10/2007 | Rajaram et al. | 60/274 |
| 2004/0238410 A1 | 12/2004 | Inoue et al. | 208/213 |
| 2005/0205423 A1 | 9/2005 | Imanaka et al. | 204/431 |
| 2006/0293169 A1 | 12/2006 | Srinivasan et al. | 502/60 |
| 2007/0042906 A1 * | 2/2007 | Pitts et al. | 502/350 |
| 2007/0166226 A1 | 7/2007 | Holmes et al. | 423/659 |
| 2007/0210349 A1 | 9/2007 | Lu et al. | 257/252 |
| 2007/0256978 A1 | 11/2007 | Stucky et al. | 210/660 |

FOREIGN PATENT DOCUMENTS

| | | |
|---|---|---|
| EP | 1832345 A1 | 9/2007 |
| WO | WO 2006/046964 A2 | 5/2006 |

OTHER PUBLICATIONS

Thiele, et al "High temperature LGS SAW gas sensor," Science Direct, Sensors and Actuators B 113 (2006) 816-822.
Haruta, "Nanoparticulate Gold Catalysts for. Low-Temperature CO Oxidation," J. of New Materials for Electrochemical Systems 7, 163-172 (2004).
Yang, et al "Generalized Syntheses of large-pore mesoporous metal oxides with semicrystalline frameworks," Letters to Nature, vol. 396, Nov. 1998.
Fan, et al "Nanoparticle Assembly of Ordered Multicomponent Mesostructured Metal Oxides via a Versatile Sol-Gel Process," Chemistry of Materials, 2006. 18 (26) 6391-6396.
Cheng, "High temperature Langasite BAW gas sensor based on ZnO nanowire arrays," 2007 IEEE Ultrasonics Symposium.
Brunelle, "Preparation of Catalysts by Metallic Complex Adsorption on Mineral Oxides," Pure & Appl. Chem. vol. 50, pp. 1211-1229, 1978.

(Continued)

*Primary Examiner* — Brian J Sines
(74) *Attorney, Agent, or Firm* — Michael W. Russell

(57) ABSTRACT

A mesoporous, transition metal oxide material having an average pore diameter ranging from 2 to 20 nm, a basic surface character defined by an isoelectric point>pH 7, and a specific surface area greater than 50 m$^2$/g can be incorporated into a NO$_x$ sensing device as a NO$_x$ film. The mesoporous, transition metal oxide material includes an oxide of yttrium, lanthanum and/or cerium, and can be formed using a surfactant-templated self-assembly process.

9 Claims, 16 Drawing Sheets

(56) References Cited

OTHER PUBLICATIONS

Schmitz, et al, "NO and $NO_2$ Adsorption on Barium Oxide: Model Study of the Trapping Stage of $NO_2$ Conversion via Lean $NO_x$ Traps," J. Phys. Chem. B 2002, 106, 4172-4180.

Sasahara, et al, "Macroporous and nanosized ceramic films prepared by modified sol-gel method with PMMA microsphere templates," Journal of the European Ceramic Society 24 (2004) 1961-1967.

Seh, et al, "Bulk acoustic wave resonator as a sensing platform for $NO_x$ at high temperatures," Sensors and Actuators B 108 (2005) 547 - 552.

China Office Action and Search Report received on May 16, 2013 from Shanghai Patent & Trademark Law Office LLC.

* cited by examiner (comparative)

(comparative)

NOX ADSORPTIVE FILMS FOR NOX SENSOR TECHNOLOGIES

BACKGROUND AND SUMMARY

The invention relates to materials suitable for use in low cost, mass sensitive $NO_x$ sensors and methods for making such materials. The invention relates also to $NO_x$ sensors incorporating such materials and which can be used, for example, in mobile diesel and lean burn gasoline engines.

Legislative standards are tightening the allowable $NO_x$ emissions levels from vehicles using mobile diesel and lean burn gasoline engines. In view of the stricter standards, it would be advantageous to monitor and control emissions for compliance, e.g., using on-board diagnostics. Indeed, proposed On Board Diagnostics (ODD) regulations would require automakers to manufacture vehicles with real-time $NO_x$ monitoring, which could lead to improved engine performance, reduced emissions and substantial cost savings. One approach to optimizing performance and reducing emissions is to supply accurate ammonia dosing based on real-time NO and $NO_2$ measurements. The various applications of $NO_x$ sensors, however, pose a challenge to engine manufacturers and sensor OEMs due to different requirements in terms of sensitivity, detection speed, and durability.

Commercial $NO_x$ sensors are known. In a typical commercial system, the principle of operation involves converting NO and $NO_2$ into oxygen, and detecting the change in oxygen content via permeation through an oxygen membrane such as a yttria-stabilized zirconia (YSZ) membrane. However, conventional commercial systems are relatively large and expensive and tend to exhibit shortcomings with respect to durability, sensitivity, particularly at low ppm levels, and selectivity (e.g., the ability to differentiate between $NO_x$ and $NH_3$).

In view of the foregoing, it would be advantageous to develop a low cost $NO_x$ sensor platform, including a $NO_x$ sensing material having improved durability, sensitivity and selectivity over conventional systems and materials.

These and other aspects and advantages of the invention can be achieved using a mesoporous, transition metal oxide $NO_x$ sensing material having a basic surface character and high surface area. The mesoporous transition metal oxide comprises one or more of yttrium oxide, lanthanum oxide and cerium oxide, and can be prepared using a surfactant-templated self-assembly process.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and together with the description serve to explain the principles and operations of the invention.

DETAILED DESCRIPTION

Figure 1:
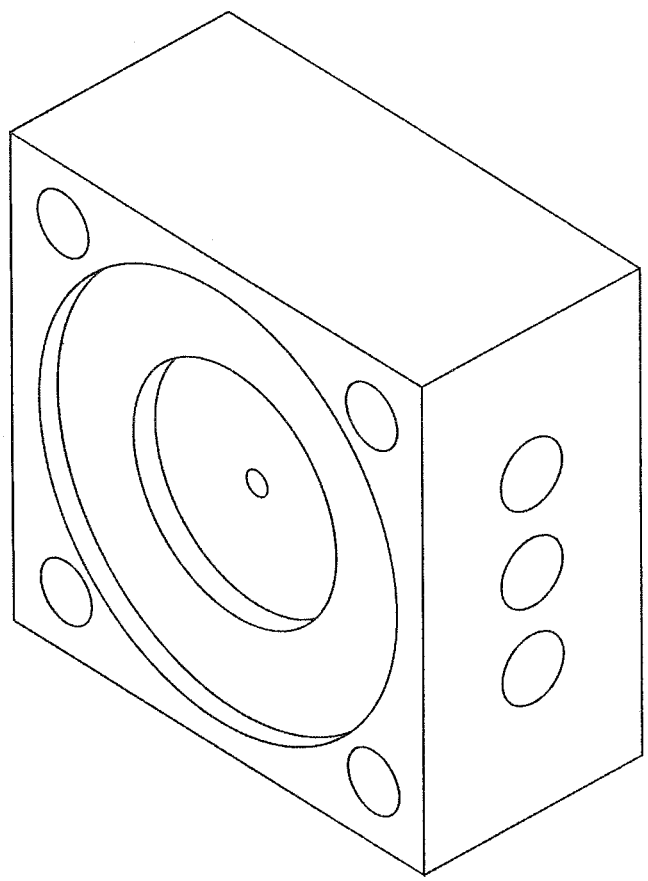
FIG. 1 shows the basic assembly of a BAW sensor fixture for high temperature gas detection.

The invention relates generally to $NO_x$ sensing materials that comprise a mesoporous, transition metal oxide having a basic surface character, high surface area, and good hydrothermal durability. The transition metal oxide can include yttrium oxide, lanthanum oxide and/or cerium oxide.

According to one embodiment, the mesoporous, transition metal oxide has an average pore diameter ranging from 2 to 20 nm, a basic surface character defined by an isoelectric point>pH 7, and a specific surface area greater than 50 $m^2/g$. According to a further embodiment, the mesoporous material is formed using a surfactant-templated self-assembly process. In a still further embodiment, a $NO_x$ sensor comprises a mesoporous, transition metal oxide film.

As used herein, the singular forms "a," "an" and "the" include plural referents unless the context clearly dictates otherwise. Thus, for example, reference to a "transition metal oxide" includes examples having two or more such "transition metal oxides" unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

A number of candidate adsorptive materials for $NO_x$ were identified based on their isoelectric points. The isoelectric point is the pH at which a solid surface carries neutral charge. The higher the isoelectric point the more basic the material surface. A number of oxide materials and their associated isoelectric points are listed in Table 1.

TABLE 1

Isoelectric points of selected metal oxides and metal carbides

| Material | Formula | Isoelectric point |
|---|---|---|
| antimony oxide | SbO3: | <1 |
| tungsten oxide | WO3: | <1 |
| vanadium oxide (vanadia) | V2O5: | 1 to 2 |
| silicon oxide (silica) | SiO2: | 1 to 3 |
| silicon carbide (alpha) | SiC: | 2-3.5 |
| tin oxide | SnO2: | 4-5.5 |
| zirconium oxide (zirconia) | ZrO2: | 4 to 7 |
| manganese oxide | MnO2: | 4 to 5 |
| titanium oxide (titania) | TiO2: | 4 to 6 |
| iron (IV) oxide | Fe3O4: | 6.5 |
| g-iron oxide | Fe2O3: | 7 |
| cerium oxide (ceria) | CeO2: | 7 |
| chromium oxide (chromia) | Cr2O3: | 7 |
| g-aluminum oxide | Al2O3: | 7 to 8 |
| thallium oxide | Ti2O: | 8 |
| a-iron oxide | Fe2O3: | 8 to 9 |
| a-aluminum oxide | Al2O3: | 8 to 9 |
| yttrium oxide (yttria) | Y2O3: | 9 |
| copper oxide | CuO: | 9.5 |
| zinc oxide | ZnO: | 9 to 10 |
| lanthanum oxide | La2O3: | 10 |
| nickel oxide | NiO: | 10 to 11 |
| magnesium oxide (magnesia) | MgO: | 12 to 13 |

In addition to a basic surface chemistry, suitable $NO_x$ sensing materials should possess adequate refractoriness, the ability to avoid hydrothermal aging (e.g., scaling), and resistance to reduction/oxidation wear, attributes that will help the materials withstand the high temperature, hydrothermal chemically aggressive environment associated with engine exhaust.

A number of transition metal oxides such as $Y_2O_3$, $La_2O_3$ and $CeO_2$ were selected based on their isoelectric point and good hydrothermal stability. These materials are interesting candidates because they span a range form weak base ($CeO_2$) to strong base ($La_2O_3$) surface chemistry.

The following materials attributes, in combination, are advantageous for the inventive $NO_x$ sensing material: (1) a basic surface character, defined by an isoelectric point>pH 7, which can attract acidic nitrogen oxides; (2) a specific surface area greater than 50 $m^2$/g, which affords sufficient dynamic range to enable acoustic wave (AW) or microelectromechanical system (MEMS) cantilever sensing platforms; and (3) a mesoporous pore structure, which provides rapid gas phase contact with the available surface area.

Thus, the $NO_x$ sensing materials according to the present invention comprise mesoporous, transition metal oxides having a basic surface character, high specific surface area, and good hydrothermal durability. In embodiments, the $NO_x$ adsorptive materials can have an isoelectric point greater than pH 7, 7.5, 8, 8.5, 9, 9.5 or 10, a specific surface area greater than 50, 75, 100, 150, 200, 250 or 300 $m^2$/g, and an average pore diameter greater than 2, 4, 8 or 16 nm. When formed into films having a thickness in the range of 0.1 to 1 micrometers, the inventive materials have an average pore diameter in the range of 2 to 20 nm, an isoelectric point in the range of 7 to 10, and a specific surface area in the range of 50 to 300 $m^2$/g. As described below, a surfactant-templated self-assembly process can be used to produce these mesoporous materials.

The inventive $NO_x$ sensing materials can be incorporated into a $NO_x$ sensor that operates, for example, on the principle of specific adsorption of NO and $NO_2$ onto a designed surface. Once adsorbed, mass sensitive detection can provide NO and $NO_2$ concentration data. Aspects of the $NO_x$ sensor include: (1) materials that are suitable for specifically adsorbing NO and $NO_2$, and which are not affected by the presence of other gases, notably carbon dioxide and water; (2) stable thin film sensor materials having a high specific surface area that enables amplification of the detectable adsorption mass; (3) operation in either a cumulative mode, where $NO_x$ is strongly bound to the surface, and whose differential is proportional to an instantaneous gas concentration, or in an equilibrium mode, where the active surface weakly binds $NO_x$, and the instantaneous surface coverage is proportional to the $NO_x$ in the gas phase; and (4) optional use of a catalyst (e.g., highly dispersed Pt) to promote rapid adhesion of $NO_x$ to the active surface and improve selectivity between NO and $NO_2$. In addition to, or in lieu of platinum, the catalyst can comprise particles of other metals, including noble metals, such as ruthenium, rhodium, palladium, silver, iridium or gold.

Changes in the oscillation frequency of a piezoelectric material can be correlated with the mass of material deposited on it vis-à-vis the Sauerbery equation, according to which the change in frequency, $$\Delta f (Hz) = -\frac{2 f_0^2}{(p_q u_q)^{1/2}} \cdot \frac{\Delta m}{A},$$

wherein $f_0$=the resonant frequency of the piezoelectric material (Hz), $\Delta m$=the change in mass (g), A=the piezoelectrically-active crystal area (area between electrodes, $m^2$), $\rho_q$=density of the piezoelectric (g/$cm^3$), $\mu_q$=shear modulus of the piezoelectric (g/cm·$s^2$), and $v_q$=transverse wave velocity of the piezoelectric (m/s). For AT-cut quartz crystal, the density is $\rho_q$=2.648 g/$cm^3$ and the shear modulus is $\mu_q$=2.947× $10^{11}$ g/cm·$s^2$).

By way of example, a $NO_x$ sensor employing a strong chemisorption interaction with $NO_x$ can be operated in a cumulative mode, where the time rate of mass change is related to the content of $NO_x$ in the gas phase. Such a device could be used up to near saturation, before the sensing surface would require regeneration, and would likely be best suited to operate in a bypass mode where a small, known flow rate of exhaust gas would impinge on the sensor material. Minimizing flow rate and maximizing sensor size would extend the time between regenerations.

By way of further example, a $NO_x$ sensor comprising a weaker binding interaction with $NO_x$ can be operated in an equilibrium mode. Lower binding strength facilitates easier regeneration. Also, if kinetics are fast, and in the limit that the binding energy is on the order of the temperature (kT), the equilibrium surface coverage will be proportional to the gas phase concentration. Such a sensor could operate continuously in a total exhaust environment. However, because coverage of the sensing surface would be temperature dependent, some provision for either isothermal conditioning of the gas, or algorithmic correction would be beneficial.

The mesoporous transition metal oxide material according to the present invention can function, for example, in a high capacity weak $NO_x$ trap. As such, in conjunction with a mass sensitive detection system, it can be useful as a $NO_x$ sensor. For instance, an acoustic wave (AW) detection system can be used to detect small mass changes in a film that result from adsorption of $NO_x$. Several configurations of AW sensing platforms could be employed for this purpose. For example, a thickness shear mode (TSM) resonator such as a quartz crystal micro-balance can be used in thin film deposition systems to measure sub-nanogram quantities of deposited film. The principle of operation involves stimulating a piezoelectric crystal and finding a resonant frequency for the induced oscillation. Because the resonant frequency is related to the effective mass of the crystal, changes in mass can be calculated from changes in resonant frequency.

Quartz has a phase transition at a relatively low temperature (573° C.). As such, other piezoelectric materials with higher temperature stability may be preferred for NO, sensing, such as gallium orthophosphate ($GaPO_4$), which is stable up to about 973° C., or materials from the families of complex oxides comprising lanthanum, gallium, silicon and oxygen (langasites), and lanthanum, gallium, tantalum and oxygen (langatites). For example, $La_3Ga_5SiO_{14}$ is stable up to its melting point of about 1470° C.

Other detection systems can also provide sensitive mass detection. Surface acoustic waves can be excited and detected by lithographically-patterned electrodes on the surface of piezoelectric substrates. The acoustic wave detection system can comprise, for example a surface acoustic wave (SAW), bulk acoustic wave (BAW) or acoustic plate mode (APM) sensor. Mass sensing can be achieved by measuring the change of surface wave velocity or attenuation caused by surface perturbations on a sensing thin film located between the electrodes. MEMS cantilevers can also show resonant response and/or deflective response based on mass changes of the cantilever.

Figure 2:
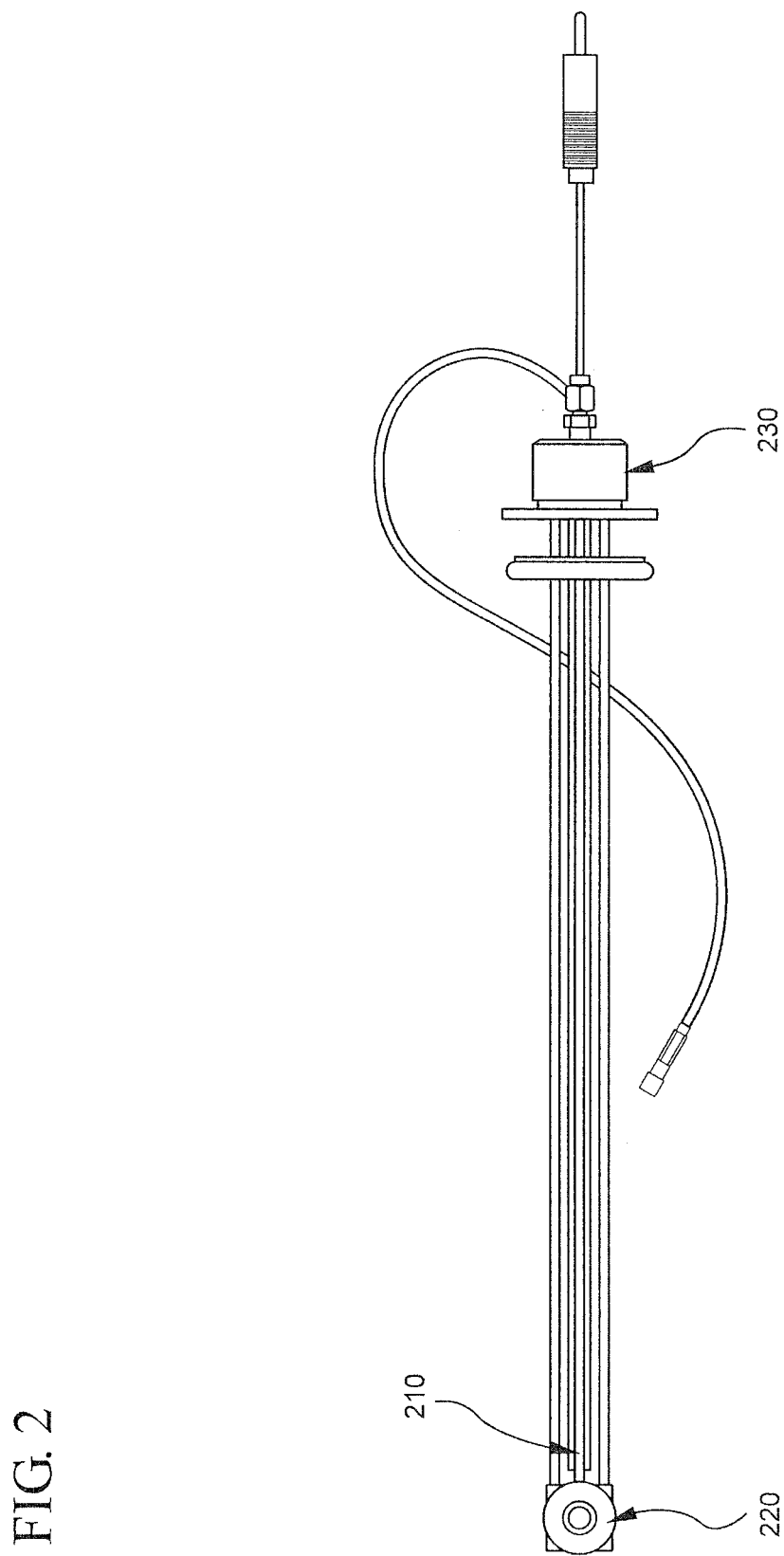
FIG. 2 shows a schematic of a BAW sensor head design.

A test platform for high temperature gas detection was based on bulk acoustic wave (BAW) sensing and included a high temperature sensor head and a QCM200 unit from Stanford Research. FIG. 1 shows the basic assembly of a BAW sensor fixture for high temperature gas detection. FIG. 2 shows a sensor head design comprising thermocouple 210, quartz crystal sensor 220, and flange 230, for easy mounting of the coated BAW device in the sensor head.

The foregoing sensing technology is potentially extremely cost effective due to the high dynamic range afforded by the low cost, high surface area, mesoporous material. Notably, adequate dynamic range on a resonant frequency device could be provided by active areas as small as 10 $mm^2$. With such a footprint, even a multi-channel array would be space effective. Further, it may also be possible to independently measure NO and $NO_2$, which would be of value in providing engine diagnostics.

Because a reduced footprint is desired together with enhanced sensitivity and selectivity, as discussed above, a sensing layer having a high effective surface area is also desired. The following calculations are illustrative of the surface area and resulting $NO_x$ loading that are achievable using the mesoporous transition metal oxide materials according to the present invention:

Consider first a sensor with 1 $cm^2$ area and a film thickness of 300 nm thick. Assuming a surface capacity of 5 $NO_2$ sites per $nm^2$, complete surface coverage on a dense oxide film would amount to a mass increase of $(5\ NO_2/nm^2)(10^{14}\ nm^2/cm^2)(mol/6.02\times10^{23}\ atoms)(46\ g/\mu mol) \approx 4\times10^{-8}\ g\ NO_2/cm^2$.

Next, consider a similar 1 $cm^2$ film having a surface area of 100 $m^2/g$ and 50% porosity. This film would provide an increased surface area of $(300\times10^{-7}\ cm^3)(7\ g/cm^3)(100\ m^2/g)(0.50)=1.05\times10^{18}\ nm^2$, and with complete monolayer coverage could load a total mass increase of $(5\ NO_2/nm^2)(1.05\times10^{18}\ nm^2/Cm^2)(mol/6.02\times10^{23}\ atoms)(46\ g/mol) \approx 4\times10^{-4}\ g\ NO_2/cm^2$.

The increased capacity provided by the mesoporous film underscores the potential to amplify the mass sensitivity of a device that would facilitate meaningful measurements from a very small sensor area.

In accordance with the present invention, mesoporous transition metal oxide materials can be prepared by forming an aqueous precursor mixture comprising a transition metal oxide precursor, a non-ionic surfactant and a solvent, drying and cross-linking the precursor mixture to form an intermediate product, and heating the cross-linked intermediate to form the oxide.

After preparing the precursor mixture, the surfactant self-assembles during a curing (heating) step to form a template for the oxide precursor, which defines a mesoscale liquid crystal phase that, upon heating and removal of the surfactant, forms a transition metal oxide sensor material that comprises domains of mesoscale porosity.

Exemplary transition metal oxide precursors include transition metal compounds of yttrium, lanthanum and cerium including, but not limited to, metal alkoxides, acetates, nitrates, sulfates, acetylacetonates, or halogenated metals.

Useful surfactants include cetyltrimethylammonium bromide (CTAB) and poly(ethylene oxide)-poly(propylene oxide)-poly(ethylene oxide) ($PEO_y$-$PPO_x$-$PEO_y$) tri-block co-polymers available from BASF, Inc. In particular, CTAB, Pluronic® F127 (x=106, y=70) and Pluronic® P123 (x=20, y=70) were used in conjunction with the disclosed inventive method. Additional non-ionic surfactants include Pluronic® F103 (x=17, y=60), Pluronic® F108 (x=127, y=50), Pluronic® F88 (x=104, y=39) and Pluronic® F65 (x=19, y=29). A precursor mixture may include one or more surfactants.

The surfactant functions as a temporary, removable organic template for the transition metal oxide precursor. The ratio of transition metal oxide precursor to surfactant, and the amount of solvent that is incorporated into the precursor mixture can be used to manipulate the self-assemblage of the surfactant through its liquid crystal phases and, in turn, the structure and properties of the resulting transition metal oxide. Specifically, the chemistry of the precursor mixture can be used to control, for example, the pore volume and pore diameter.

One or more acids may be added to the precursor mixture in order to initiate hydrolysis of the transition metal oxide precursor. Water may be indirectly added to the precursor mixture as a diluent for the acid, or as a product of the hydrolysis reaction.

In precursor mixtures comprising $PEO_y$-$PPO_x$-$PEO_y$ tri-block co-polymers, water, if present, interacts with the PEO blocks and, by swelling the phase containing the transition metal oxide precursor, can affect the self-assembly of the surfactant template. The concentration of water in the precursor mixture can be used to control the assemblage of mesoporous channels in both the cross-linked material and in the post-thermally treated product.

EXAMPLES

The invention will be further clarified by the following examples.

Example 1

Figure 16:
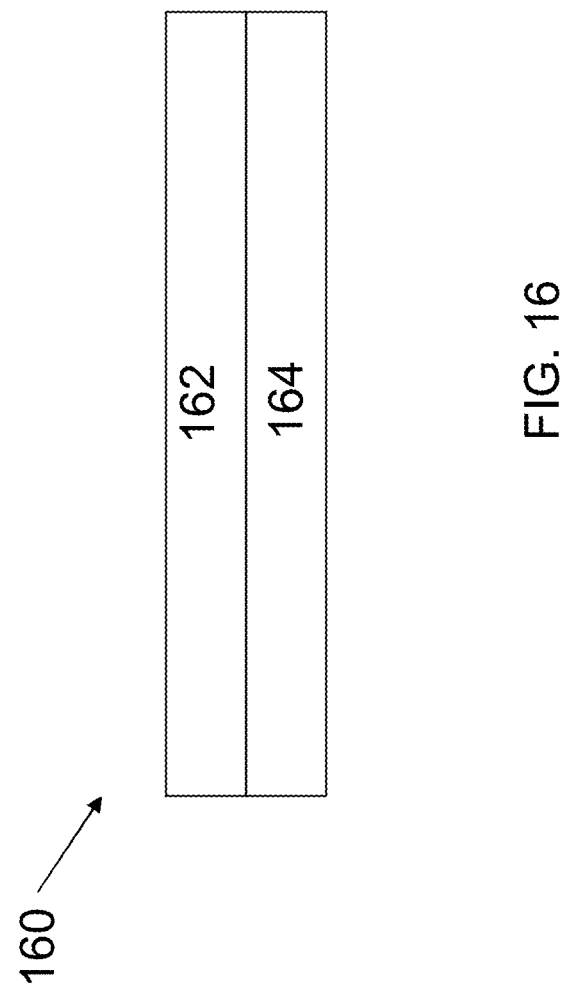
FIG. 16 shows a mesoporous thin film formed on a substrate, according to one embodiment.

Cerium acetate (3.2 g) was dissolved in a mixture of ethanol (30 grams), glacial acetic acid (2.4 grams), concentrated HCl (2 ml), and Pluronic® F127 (1.6 grams). The solution was stirred for 1 hour at room temperature. Thin film samples 160 were made by spin coating the solution onto quartz crystal substrates 164, and powder samples were made by evaporating the solvents at 40° C. overnight (FIG. 16). The thin film and powder samples were cured by heating at 65° C. for 5 days before calcining at 35° C. for 5 hours.

Figure 3:
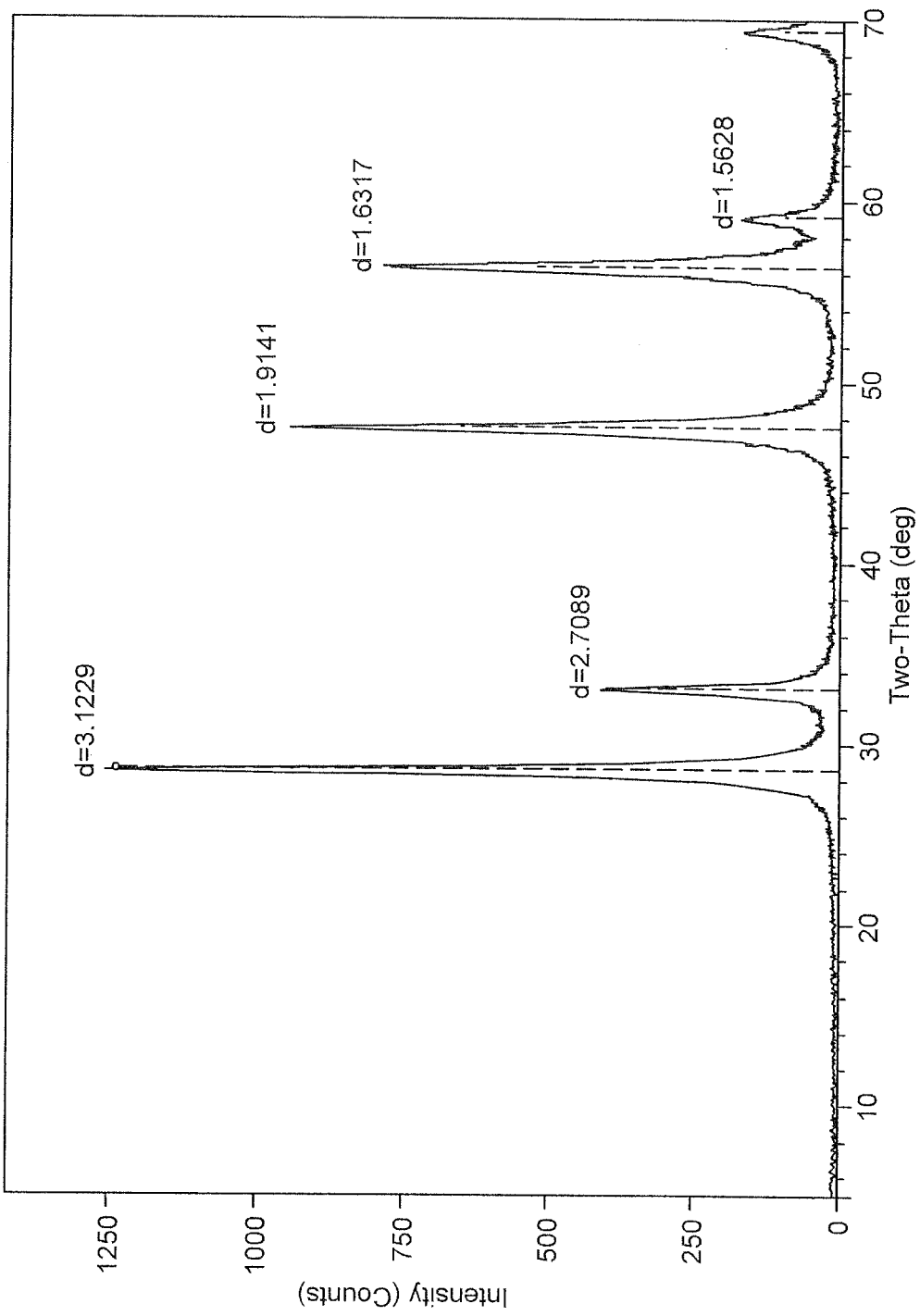
FIG. 3 is a wide-angle X-ray diffraction scan of a cerium acetate precursor-based mesoporous powder.
Figure 4:
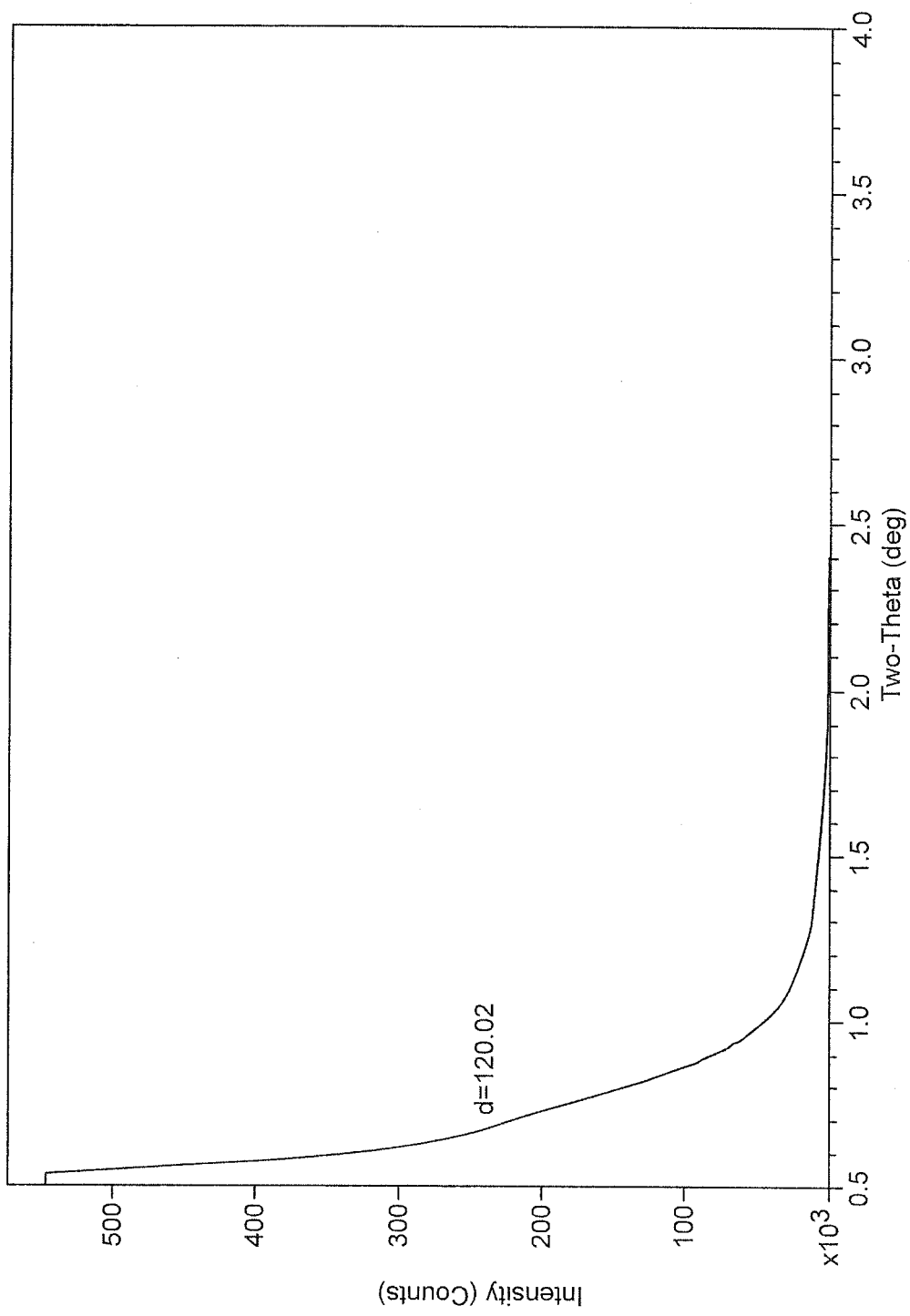
FIG. 4 is a small-angle X-ray diffraction scan of a cerium acetate precursor-based mesoporous thin film.

A wide-angle X-ray diffraction (XRD) scan of the cerium acetate precursor-based mesoporous powder after calcination at 350° C. is shown in FIG. 3, and a small angle XRD scan of a cerium acetate precursor-based mesoporous thin film after calcination at 350° C. is shown in FIG. 4. The XRD data confirm that the composition is $CeO_2$ having a mesoporous structure with a d-spacing of about 12 nm. Nitrogen porosimetry reveal a specific surface area of about 100 $m^2/g$, and a pore volume of about 50 to 60% by volume.

Example 2

$LaCl_3 \cdot 7H_2O$ (0.01 mole, 3.7 g) was dissolved in 10 ml of ethanol together with 1 g of Pluronic® P123. After stirring the solution for 30 minutes, films 162 were formed by spin coating onto quartz crystal substrates 164, and powders were formed by evaporating the solvent at 40° C. overnight. The thin film and powder samples were cured by heating at 65° C. for 5 days before calcining at 400° C. for 5 hours to form a high surface area lanthanum oxide.

The powder sample had a specific surface area of 53 $m^2/g$ and a pore volume of about 50%. A summary of specific surface area, pore volume and pore diameter data for calcined powder samples from examples 1 and 2 is shown in Table 2.

TABLE 2

BET multipoint surface area, BJH cumulative pore volume and BJH average pore diameter data for calcined powders

| Sample | surface Area [$m^2/g$] | Cumulative Pore Volume [$cm^3/g$] | Average Pore Diameter [Å] |
|---|---|---|---|
| $Ce(Ac)_3$ | 100.1 | 0.224 | 78.6 |
| $LaCl_3$ | 52.6 | 0.162 | 118.4 |

Example 3

A precursor solution comprising a mixture of 3.2 g lanthanum acetate, 0.55 g P123, 30 ml ethanol, 2.4 g glacial acetic acid, and 1 ml nitric acid is prepared and aged for 2 hours at 40° C. The solution is spin coated onto quartz substrates and heated in a covered Petri dish for 6 hours at 65° C. before calcining at 350° C. for 5 hours to form a lanthanum oxide film.

Figure 5:
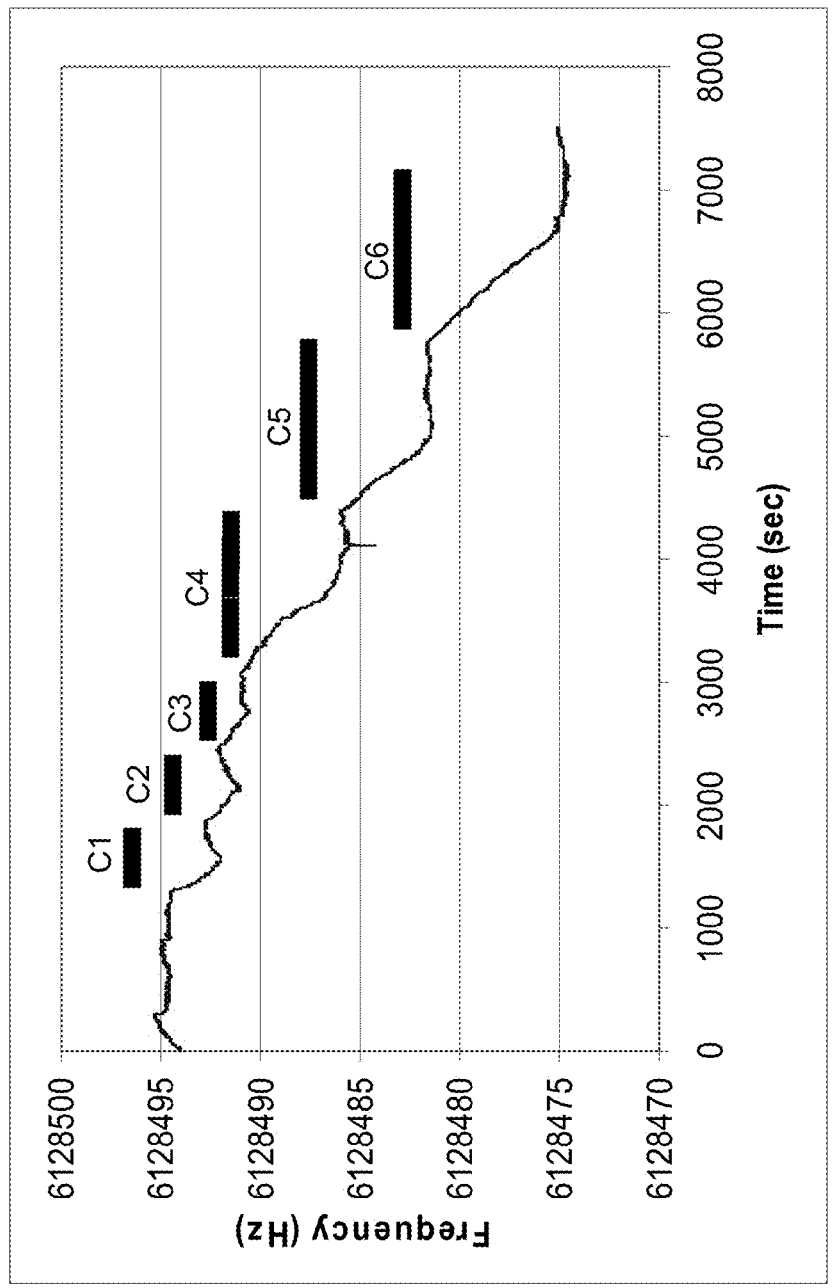
FIG. 5 shows the frequency response of a $La_2O_3$-coated quartz sensor.

FIG. 5 shows the frequency response of a $La_2O_3$-coated quartz sensor to successive on-off $NO_2$ exposure at a constant temperature of 200° C. In the following frequency versus time plots, the coated substrate is placed within a quartz tube (approximately 1 inch ID, 24 inches long) that is positioned with a programmable furnace. The flow of gas through the tube is controlled such that, with reference to the figures, the first 50% of the illustrated "cycle" bar represents $NO_2$ "on" time, while the second 50% of the "cycle" bar represents $NO_2$ "off" time. In the figures, successive "on/off" cycles are abbreviated C1, C2, etc.

With reference to FIG. 5, when the $NO_2$ flow is turned on (500 ppm in 0.5 l/min total flow), the resonant frequency decreases due to $NO_2$ adsorption by the $La_2O_3$ film. The adsorption of $NO_2$ creates a damping effect that decreases the resonant frequency. When the $NO_2$ flow is turned off, the frequency increases slowly or remains substantially constant during a recovery period. It should be noted that the recovery is associated merely with abatement of the $NO_2$ flow; there is no "flush" gas that aids the $NO_2$ desorption. The overall negative slope of the frequency response is consistent with incomplete desorption of $NO_2$.

Example 4

A precursor solution comprising a mixture of 14.6 ml lanthanum 2-methoxyethoxide (5 wt. % solution in 2-methoxyethanol), 0.11 g P123, 5 ml ethanol and 0.016 ml nitric acid is prepared and aged at 40° C. overnight. The solution is then spin coated onto $GaPO_4$ substrates and heated in a covered Petri dish for 1 hour at 20° C., 1 hour at 30° C., and 1 hour at 60° C., before calcining at 350° C. for 5 hours to form a lanthanum oxide film.

Figure 6:
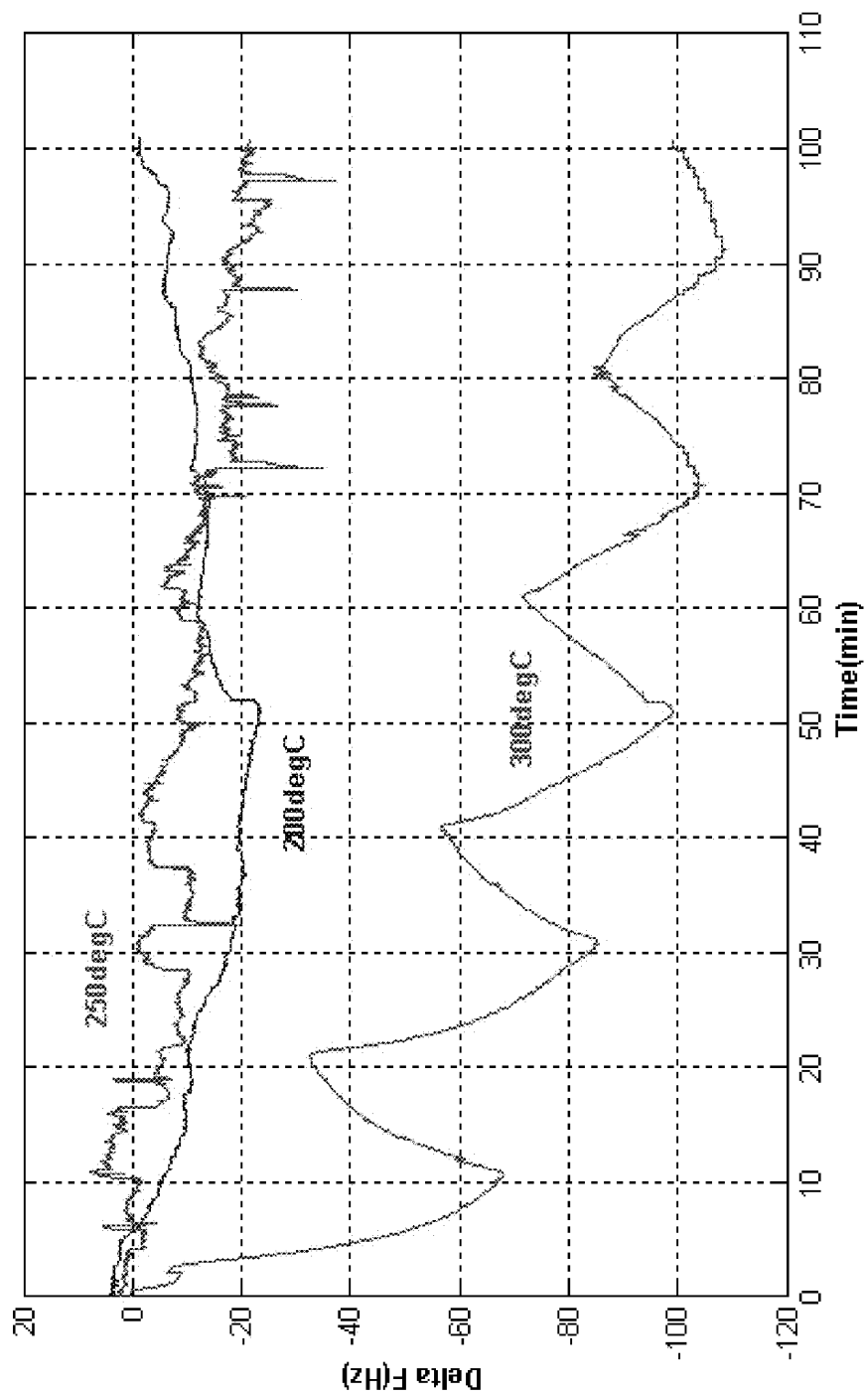
FIG. 6 shows the frequency response of $La_2O_3$-coated $GaPO_4$ sensors at 200, 250 and 300° C.

FIG. 6 shows the frequency response of $La_2O_3$-coated $GaPO_4$ crystals at 200, 250 and 300° C. to a cyclic $NO_2$ flow of 500 ppm $NO_2$ at 0.5 l/min total flow. Virtually no response is observed at 200° C. or 250° C. At a temperature of 300° C., however, the results showed $NO_2$ adsorption (with incomplete desorption) during each on/off cycle.

The sensitivity of the $GaPO_4$ sensor can be expressed as a ratio of the observed frequency change the change in mass per unit area or, expressed as a differential, as $S=df/d\rho_s=82.24$ $Hz\text{-}cm^2/mg$. For a frequency range, $\Delta f=20\text{-}70$ Hz, the adsorbed mass is estimated to be 0.25-0.9 $mg/cm^2$.

Example 5

Comparative

A comparative precursor solution comprising a mixture of 4.64 ml cerium 2-methoxyethoxide (20 wt. % solution in 2-methoxyethanol), 5 ml ethanol, 7.5 ml 2-methoxyethanol and 0.016 ml nitric acid is prepared and aged at 40° C. overnight. The solution is then spin coated onto $GaPO_4$ substrates and heated in a covered Petri dish for 1 hour at 20 C, 1 hour at 30° C., and 1 hour at 60° C., before calcining at 350° C. for 5 hours to form a cerium oxide film. The comparative precursor solution does not include a surfactant.

Figure 7:
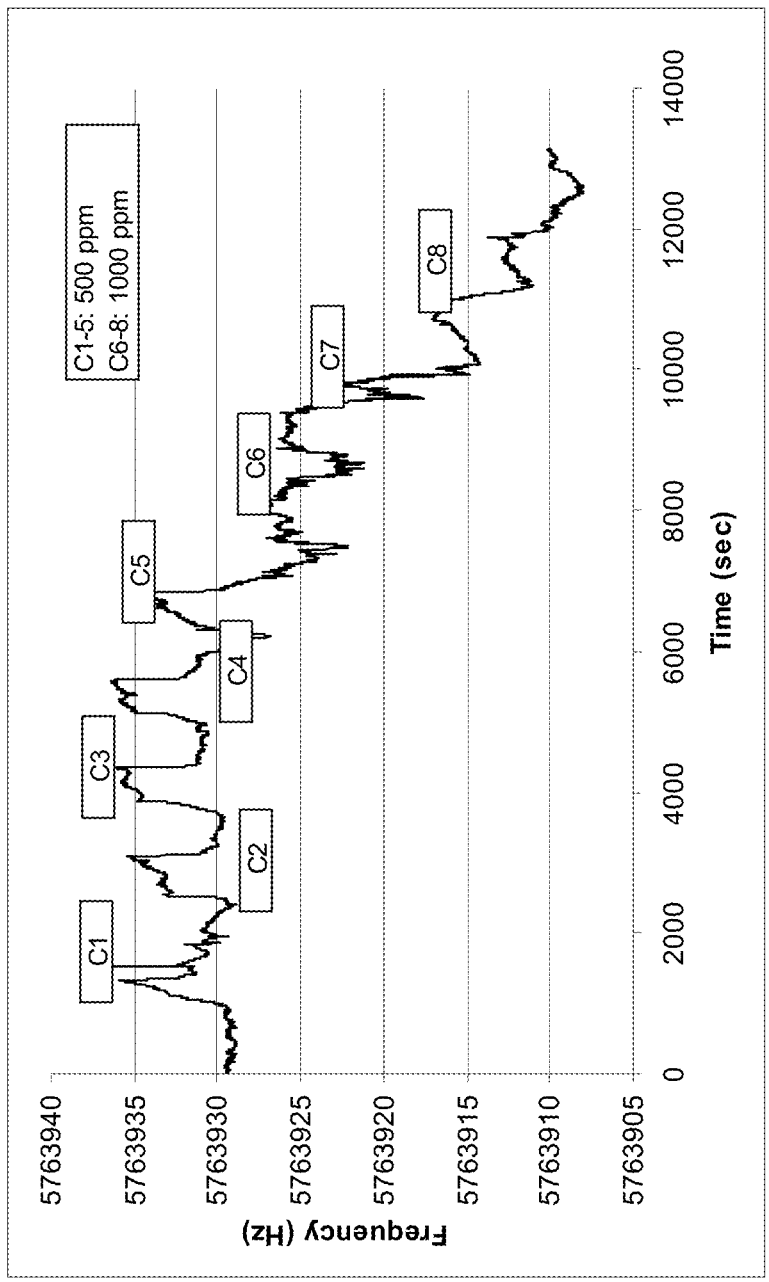
FIG. 7 shows the frequency response of a comparative $CeO_2$-coated $GaPO_4$ sensor at 300° C.

FIG. 7 shows the frequency response of $CeO_2$-coated $GaPO_4$ crystals at 300° C. to a cyclic $NO_2$ flow of 500 ppm $NO_2$ (cycles 1-5) and 1000 ppm $NO_2$ (cycles 6-8) at 0.5 l/min total flow. The results showed fairly rapid (<1 min) $NO_2$ adsorption, though after the third cycle, the frequency response is increasingly irregular. Through the first three cycles, the frequency response is only about 5 Hz.

Example 6

Comparative

A comparative precursor solution comprising a mixture of 12.6 ml yttrium 2-methoxyethoxide (5 wt. % solution in 2-methoxyethanol), 5 ml ethanol, and 0.016 ml nitric acid is prepared and aged at 40° C. overnight. The solution is spin coated onto $GaPO_4$ substrates and heated in a covered Petri dish for 1 hour at 20° C., 1 hour at 30° C., and 1 hour at 60° C., before calcining at 350° C. for 5 hours to form a yttrium oxide film. The comparative precursor solution does not include a surfactant.

Figure 8:
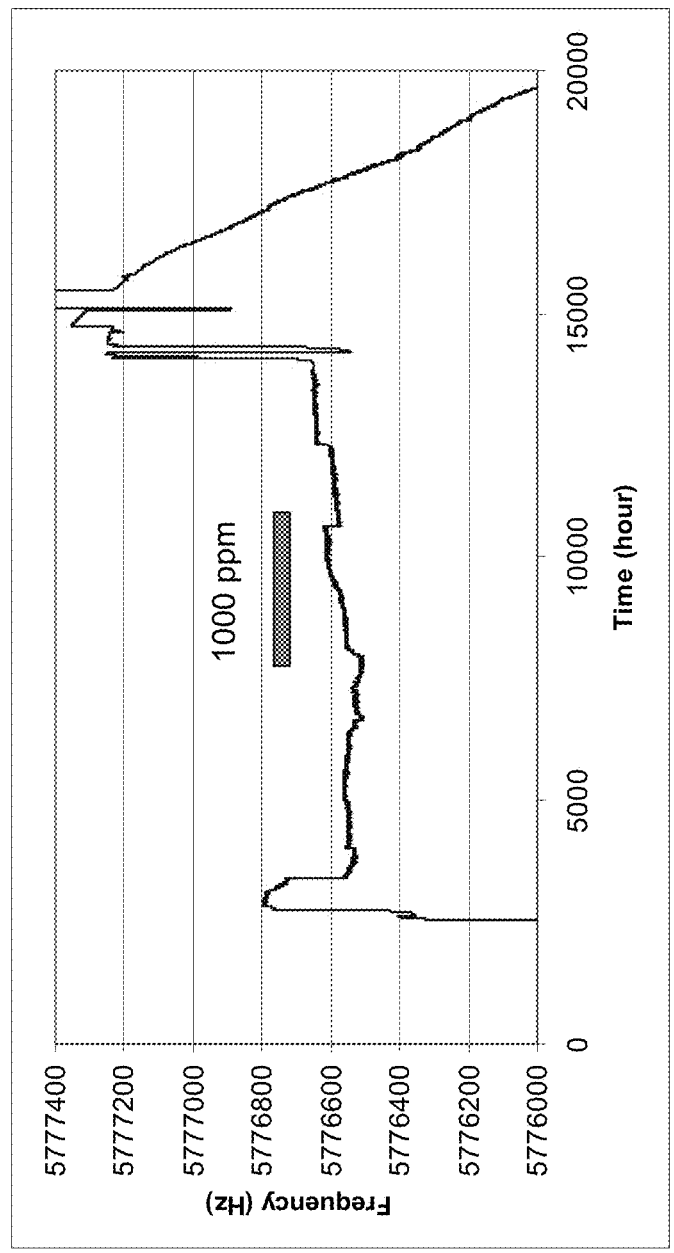
FIG. 8 shows the frequency response of a comparative $Y_2O_3$-coated $GaPO_4$ sensor at 300° C.

FIG. 8 shows the frequency versus time plot of $Y_2O_3$-coated $GaPO_4$ crystals at 300° C. There is no measurable response to the cyclic $NO_2$ flow.

Example 7

A precursor solution comprising a mixture of 7.3 ml lanthanum 2-methoxyethoxide (5 wt. % solution in 2-methoxyethanol), 0.135 g CTAB (cetyltrimethylammonium bromide), 5 ml ethanol and 0.016 ml nitric acid is prepared and aged at 40° C. overnight. The solution is then spin coated onto $GaPO_4$ substrates and heated in a covered Petri dish for 1 hour at 40° C. and 1 hour at 90° C. before calcining at 400° C. for 4 hours to form a lanthanum oxide film.

Figure 9:
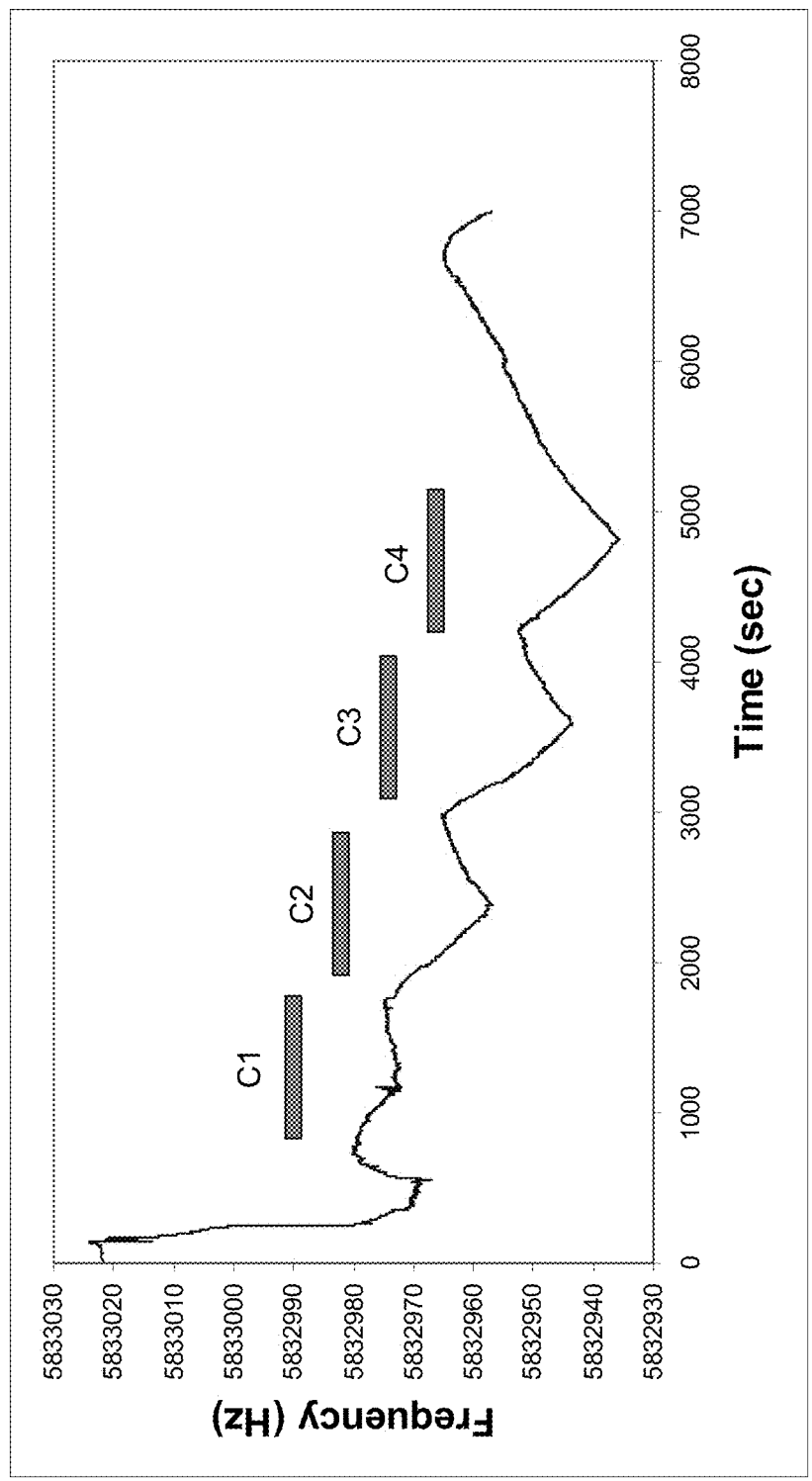
FIG. 9 shows the frequency response of a $La_2O_3$-coated $GaPO_4$ sensor at 300° C.
Figure 10:
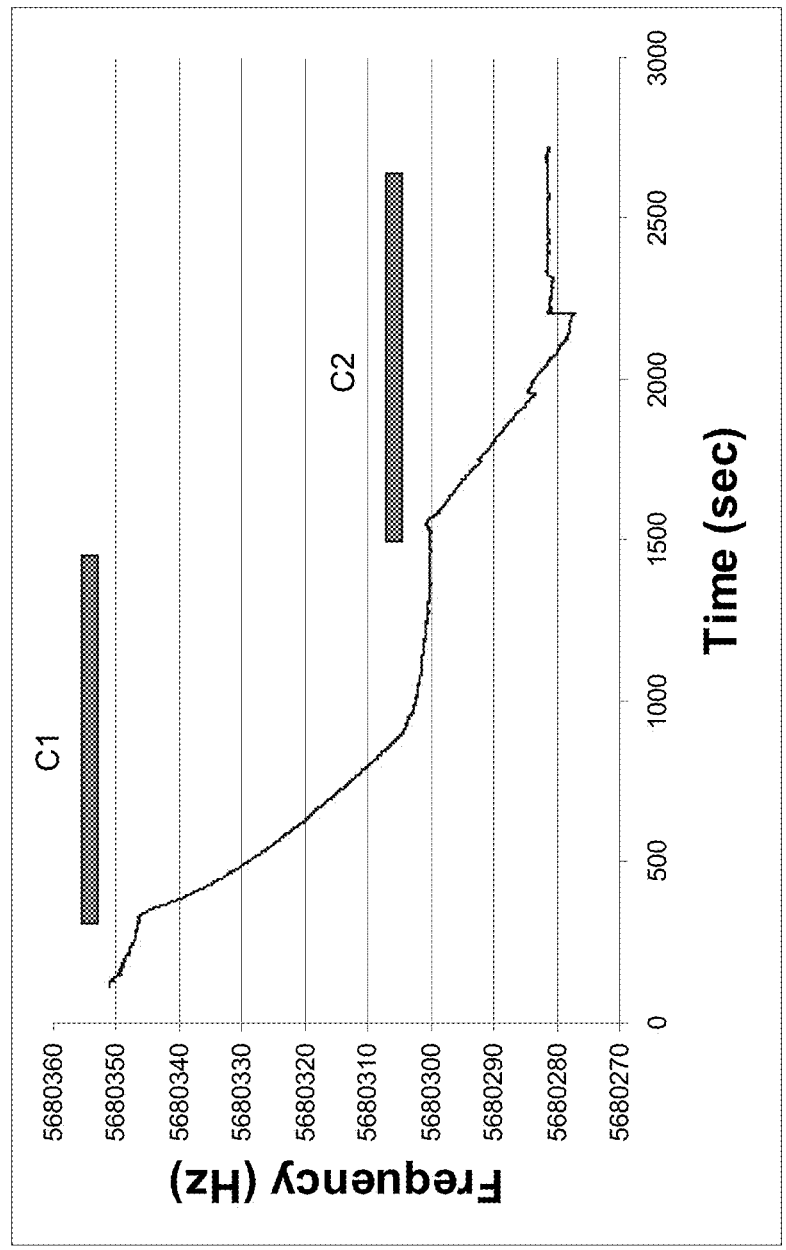
FIG. 10 shows the frequency response of a $La_2O_3$-coated $GaPO_4$ sensor at 250° C.
Figure 11:
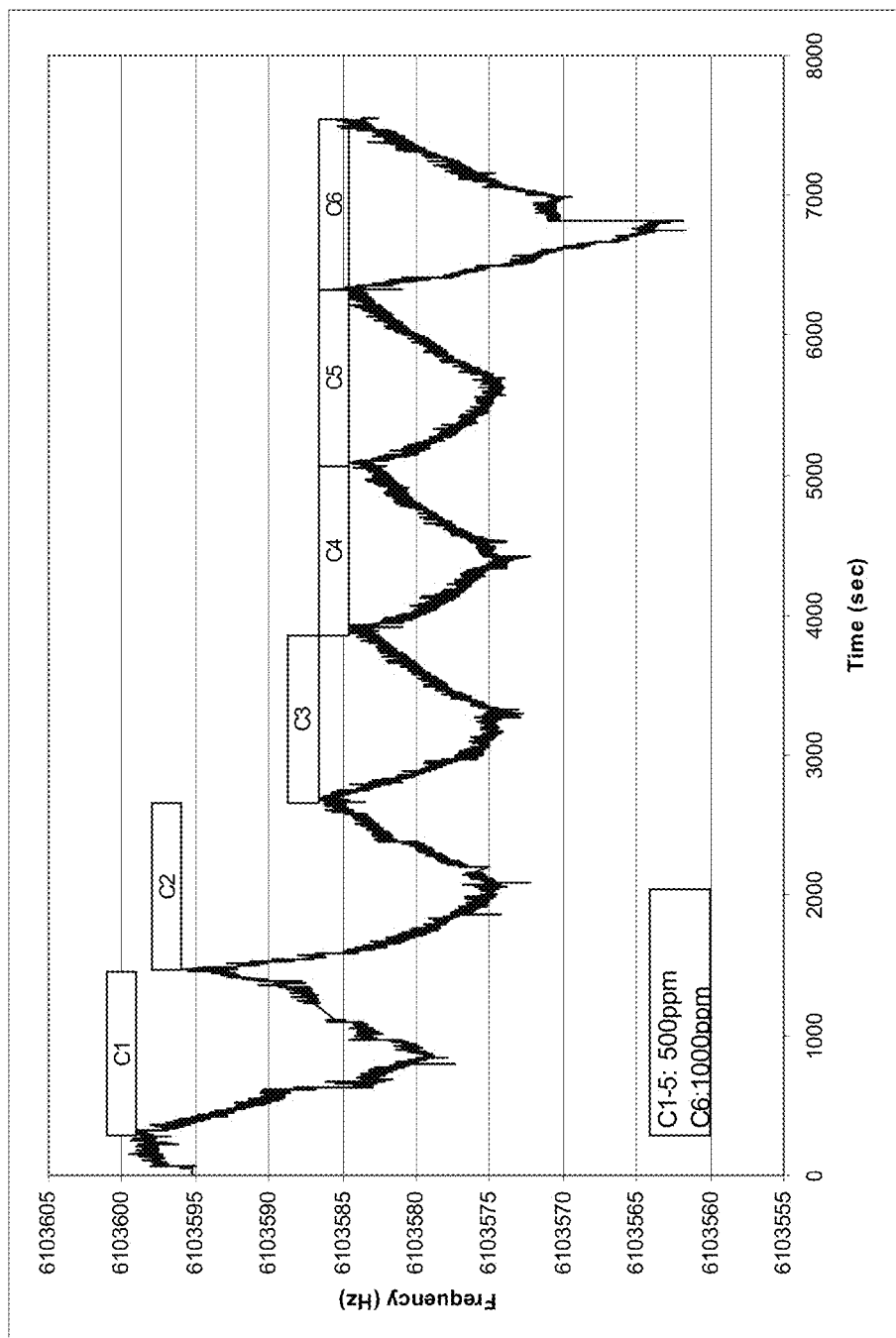
FIG. 11 shows the frequency response of a $La_2O_3$-coated $GaPO_4$ sensor at 300° C.
Figure 12:
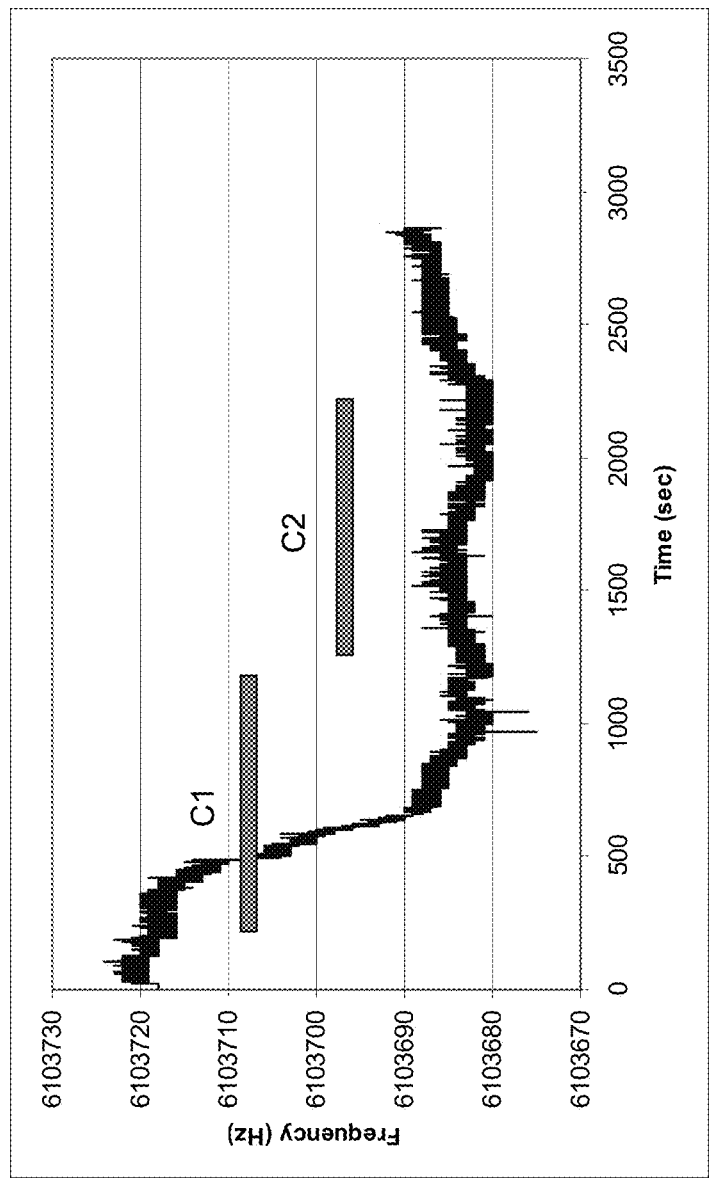
FIG. 12 shows the frequency response of a $La_2O_3$-coated $GaPO_4$ sensor at 350° C.
Figure 13:
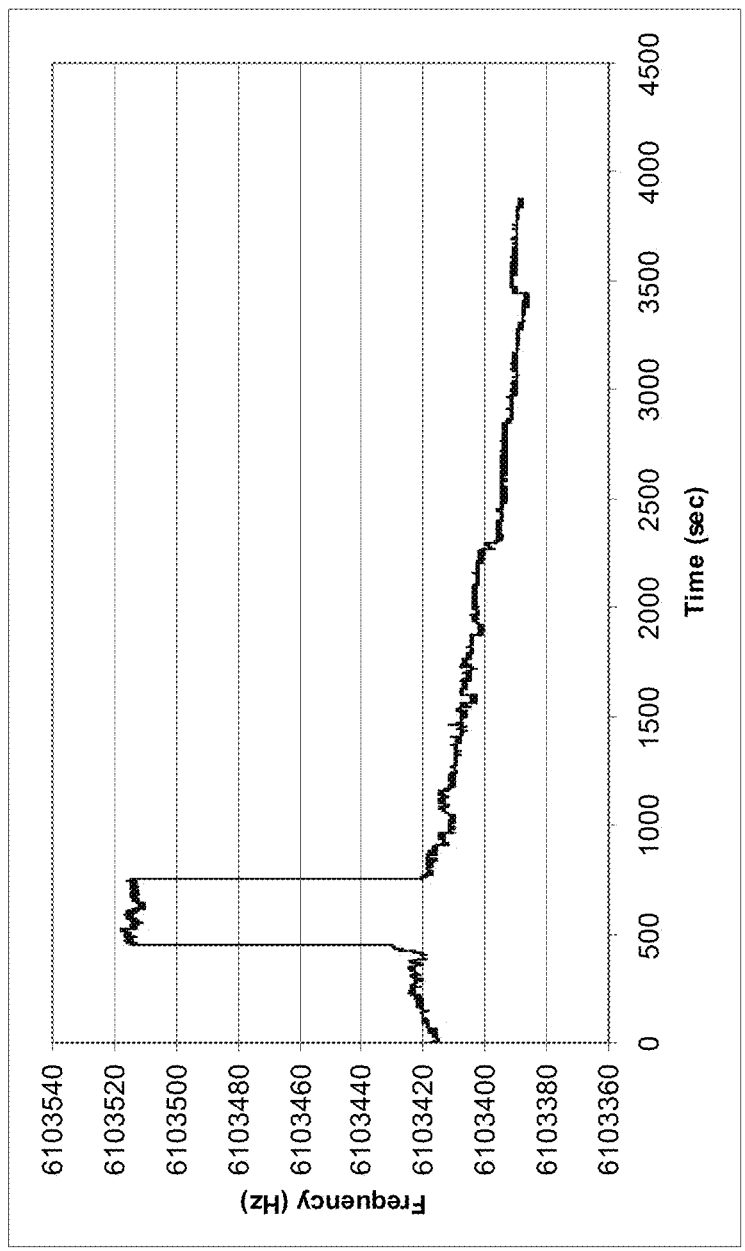
FIG. 13 shows the frequency response of a $La_2O_3$-coated $GaPO_4$ sensor at 400° C.

FIG. 9 shows the frequency response of $La_2O_3$-coated $GaPO_4$ crystals at 300° C. to a 500 ppm $NO_2$ (0.5 l/min total flow) cyclic $NO_2$ flow. The frequency response is reproducible for the first four cycles ($\Delta f$~10-20 Hz) showing an intercycle recovery of about 50%, which is consistent with irreversible adsorption.

Example 8

A precursor solution comprising a mixture of 7.3 ml lanthanum 2-methoxyethoxide (5 wt. % solution in 2-methoxyethanol), 0.15 g P123, 5 ml ethanol and 0.016 ml nitric acid is prepared and aged at 40° C. overnight. The solution is spin coated onto $GaPO_4$ substrates and heated in a covered Petri dish for 1 hour at 40° C. and 1 hour at 90° C. before calcining at 400° C. for 4 hours to form a lanthanum oxide film.

FIGS. 10-13 show the frequency response to cyclic $NO_2$ flow of $La_2O_3$-coated $GaPO_4$ crystals at 250, 300, 350 and 400° C., respectively. In this sequence of figures, a single sample is tested first at 300° C. (FIG. 11), and then at 350, 400 and 250° C. At 300° C., the frequency response ($\Delta f$~10 Hz) is reproducible for at least six cycles with nearly 100% recovery between cycles 3 and 5. A 500 ppm $NO_2$ (0.5 l/min total flow) cyclic $NO_2$ flow is used for cycles 1-5, while the $NO_2$ flow is increased to 1000 ppm in cycle 6.

At 350 and 400° C. (FIG. 12 and FIG. 13), there is no significant response to the cyclic $NO_2$ flow. The signal jump in the 400° C. data (FIG. 13) is a measurement artifact. At 250° C. (FIG. 10), there is relatively strong adsorption ($\Delta f$~20-40 Hz), but weak desorption.

Example 9

A precursor solution comprising a mixture of 7.3 ml lanthanum 2-methoxyethoxide (5 wt. % solution in 2-methoxyethanol), 0.5 g P123, 5 ml ethanol and 0.016 ml nitric acid is prepared and aged at 40° C. overnight. The solution is spin coated onto $GaPO_4$ substrates and heated in a covered Petri dish for 1 hour at 40° C. and 1 hour at 90° C. before calcining at 400° C. for 4 hours to form a lanthanum oxide film.

Figure 14:
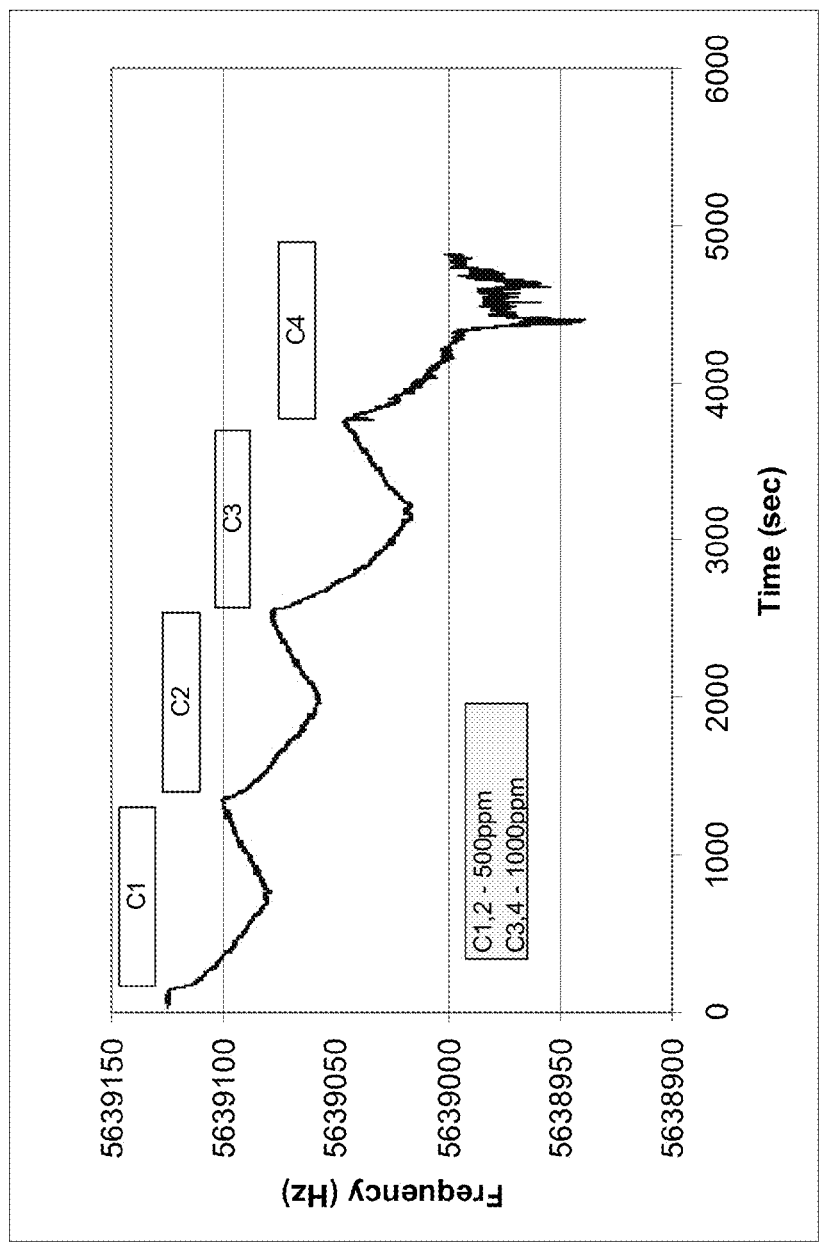
FIG. 14 shows the frequency response of a $La_2O_3$-coated $GaPO_4$ sensor at 300° C.

FIG. 14 shows the frequency response of $La_2O_3$-coated $GaPO_4$ crystals at 320° C. to a cyclic $NO_2$ flow of 500 ppm $NO_2$ (cycles 1 and 2) and 1000 ppm $NO_2$ (cycles 3 and 4) at 0.5 l/min total flow. The frequency response is relatively strong (~50 Hz for cycles 1 and 2, and ~75 Hz for cycles 3 and 4), with about 50% recovery between cycles.

Example 10

A precursor solution comprising a mixture of 7.3 ml lanthanum 2-methoxyethoxide (5 wt. % solution in 2-methoxyethanol), 0.5 g P123, 5 ml ethanol and 0.016 ml nitric acid is prepared and aged at 40° C. overnight. The solution is spin coated onto langasite substrates and heated in a covered Petri dish for 1 hour at 40° C. and 1 hour at 90° C. before calcining at 400° C. for 4 hours to form a lanthanum oxide film.

Figure 15:
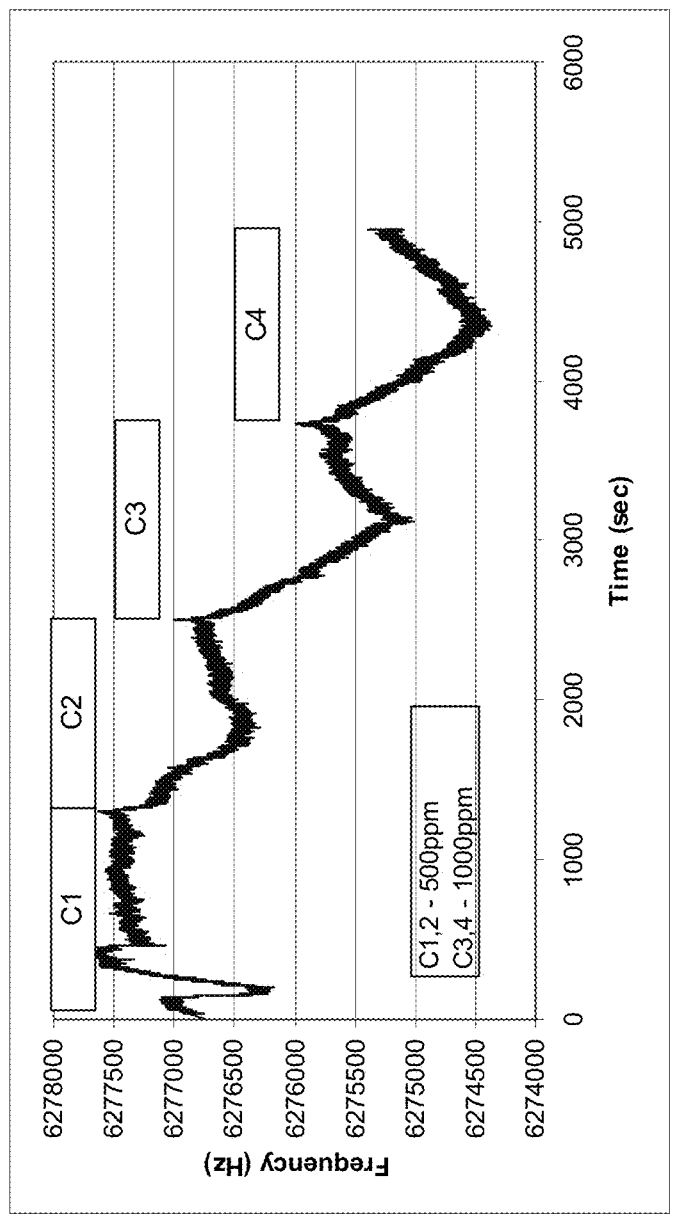
FIG. 15 shows the frequency response of a $La_2O_3$-coated langasite sensor at 300° C.

FIG. 15 shows the frequency response of $La_2O_3$-coated langasite crystals at 300° C. to a cyclic $NO_2$ flow of 500 ppm $NO_2$ (cycles 1 and 2) and 1000 ppm $NO_2$ (cycles 3 and 4) at 0.5 l/min total flow. The frequency response on the langasite substrates is strong (~1000 Hz for cycles 1 and 2, and ~1500 Hz for cycles 3 and 4) compared with $La_2O_3$-coated $GaPO_4$ crystals (~50-75 Hz), and shows good reproducibility after the first cycle. As with the previous examples, the downward shift in the baseline is attributable to incomplete desorption. There is a recovery between cycles of about 50%.

A summary of the samples, their preparation protocol, and the corresponding test results (frequency response and nominal % recovery) is shown in Table 3 for examples 3-10.

TABLE 3

Sample and Test Result Summary

| Ex. | Precursor | Surfactant | Surfactant (g)/0.01 mole precursor | Substrate | Aging | Calcination | Result |
|---|---|---|---|---|---|---|---|
| 3 | La (acetate) | P123 | 0.55 | Quartz | 65/5 hrs | 350 C./6 hrs | |
| 4 | La (methoxyethoxide) | P123 | 0.55 | $GaPO_4$ | 20 C./1 hr, 30 C./1 hr, 60 C./1 hr | 350 C./5 hrs | 12-70 Hz |
| 5* | Ce (methoxyethoxide) | None | NA | $GaPO_4$ | 20 C./1 hr, 30 C./1 hr, 60 C./1 hr | 350 C./5 hrs | ~5 Hz |
| 6* | Y (methoxyethoxide) | None | NA | $GaPO_4$ | 20 C./1 hr, 30 C./1 hr, 60 C./1 hr | 350 C./5 hrs | No response |
| 7 | La (methoxyethoxide) | CTAB | 1.25 | $GaPO_4$ | 40 C./1 hr, 90 C./1 hr | 400 C./4 hrs | 10-20 Hz |
| 8 | La (methoxyethoxide) | P123 | 1.5 | $GaPO_4$ | 40 C./1 hr, 90 C./1 hr | 400 C./4 hrs | 10-20 Hz |
| 9 | La (methoxyethoxide) | P123 | 5 | $GaPO_4$ | 40 C./1 hr, 90 C./1 hr | 400 C./4 hrs | 50-75 Hz |
| 10 | La (methoxyethoxide) | P123 | 5 | Langasite | 40 C./1 hr, 90 C./1 hr | 400 C./4 hrs | >1000 Hz |

*Examples 5 and 6 are comparative.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. A mesoporous, oxide thin film having an average pore diameter ranging from 2 to 20 nm, a basic surface character defined by an isoelectric point>pH 7, and a specific surface area greater than 50 $m^2/g$, wherein the oxide is selected from the group consisting of yttrium oxide, lanthanum oxide, and mixtures thereof, wherein the thin film is formed on a substrate and the substrate is formed from a material selected from the group consisting of gallium orthophosphate, langasites, and langatites, and the film further includes dispersed particles of a catalyst.

2. A $NO_x$ sensor comprising the film of the mesoporous oxide of claim 1.

3. A $NO_x$ sensor comprising a mesoporous oxide film, wherein the oxide is selected from the group consisting of yttrium oxide, lanthanum oxide, and mixtures thereof, and the film is formed on a substrate and the substrate is formed from a material selected from the group consisting of gallium orthophosphate, langasites, and langatites, wherein the film further includes dispersed particles of a catalyst.

4. The $NO_x$ sensor of claim 3, wherein the catalyst comprises dispersed particles of a metal selected from the group consisting of ruthenium, rhodium, palladium, silver, iridium, platinum and gold.

5. The thin film according to claim 1, wherein the thin film comprises domains of mesoscale porosity.

6. The $NO_x$ sensor of claim 3, wherein the thin film comprises domains of mesoscale porosity.

7. The thin film according to claim 1, wherein the mesoporous oxide has a specific surface area greater than 50 $m^2/g$.

8. The thin film according to claim 1, wherein the mesoporous oxide has an average pore diameter greater than 2 nm.

9. The thin film according to claim 1, wherein the thin film has a pore volume of about 50 to 60% by volume.

* * * * *